United States Patent [19]
Auner

[11] Patent Number: 5,919,416
[45] Date of Patent: Jul. 6, 1999

[54] STERILIZATION PROCESS FOR THERMOPLASTIC APPLIANCES

[76] Inventor: J. David Auner, P.O. Box 85, 128 Russell St., Ironton, Mo. 63650

[21] Appl. No.: 08/978,134

[22] Filed: Nov. 25, 1997

[51] Int. Cl.⁶ .................. A61L 2/12; A61L 2/20
[52] U.S. Cl. .................. 422/26; 422/21; 422/28; 422/297; 422/298; 422/300; 422/305; 206/368; 206/63.5; 206/823; 132/308
[58] Field of Search .................. 422/21, 24, 26, 422/28, 292, 295, 297, 298, 300, 305; 206/368, 369, 63.5, 823; 132/308

[56] References Cited

U.S. PATENT DOCUMENTS

| | | | |
|---|---|---|---|
| 3,955,922 | 5/1976 | Moulthrop | 422/24 |
| 4,400,357 | 8/1983 | Hohmann | 422/300 |
| 4,406,861 | 9/1983 | Beauvais et al. | 422/113 |
| 5,019,344 | 5/1991 | Kutner et al. | 422/21 |
| 5,019,359 | 5/1991 | Kutner et al. | 422/294 |
| 5,040,260 | 8/1991 | Michaels | 15/167.1 |
| 5,124,125 | 6/1992 | Brent | 422/26 |
| 5,126,572 | 6/1992 | Chu | 250/455.11 |
| 5,164,166 | 11/1992 | Stepanski et al. | 422/297 |
| 5,166,528 | 11/1992 | Le Vay | 250/455.11 |
| 5,248,478 | 9/1993 | Kutner et al. | 422/21 |
| 5,253,927 | 10/1993 | Erickson | 300/2 |
| 5,340,200 | 8/1994 | Erickson | 300/2 |
| 5,413,757 | 5/1995 | Kutner et al. | 422/21 |
| 5,690,852 | 11/1997 | Saito et al. | 422/21 |
| 5,697,291 | 12/1997 | Burgener et al. | 422/21 |
| 5,792,421 | 8/1998 | Riley | 422/21 |

OTHER PUBLICATIONS

Special Report; Toothbrush contamination: a potential health risk?; Richard T. Glass, D.D.S., Ph.D./Mary Martin Lare, R.D.H., D.D.S.; Quintessence International vol. 17, No. 1/1986, pp. 39–42.

Dental Research; Transmission of disease in dogs by toothbrushing; Richard T. Glass, D.D.S. Ph.D./Mary Lare, R.D.H., D.D.S.; Quintessence International vol. 20, No. 11/1989, pp. 819–824.

Special Report; More on the contaminated toothbrush: the viral story; Richard T. Glass, DDS, PhD/Harold G. Jensen, PhD; Quintessence International; vol. 19, No. 10/1988; pp. 713–716.

Oral Pathology; Richard T. Glass, DDS, PhD; toothbrush types and retention of microorganisms; how to choose a biologically sound toothbrush; ODA Journal; Winter 1992.

Article 4 Continuing Education; The Infected Toothbrush, the Infected Denture, and Transmission of Disease: A Review; Compend Contin. Educ. Dent, vol. XIII, No. 7; pp. 592, 594, 596–598 No Date Availabe.

ODA Journal; Summer 1992; p. 30.

(List continued on next page.)

*Primary Examiner*—Elizabeth McKane
*Assistant Examiner*—Fariborz Moazzam
*Attorney, Agent, or Firm*—Nixon & Vanderhye P.C.

[57] ABSTRACT

An appliance which is entirely, or includes components, formed of a thermoplastics material, e.g., conventional nylon-bristle toothbrushes, may be sterilized by first bringing water contained in a reservoir of an uncovered sterilization tray to, or near, its boiling point by initial exposure to microwave energy. Thereafter, the appliance is placed in the sterilization tray in proximity to the microwave-preheated water. The sterilization tray may then be covered and subjected to an additional (shorter) cycle of microwave energy. During this subsequent microwave cycle, the water in the reservoir boils so that steam fills the covered container and is pressurized to less then about 10 psig (e.g., due to the fluid-tight seal formed by the container's cover). The steam and the microwave energy are sufficient to sterilize the toothbrush bristles.

26 Claims, 1 Drawing Sheet

OTHER PUBLICATIONS

Oral Pathology; Richard T. Glass, DDS, PhD/Harold G. Jensen, PhD; the effectiveness of a U–V toothbrush sanitising device in reducing the number of bacteria, yeasts and viruses on toothbrushes; ODA Journal; Sring 1994; pp. 24–28.

Oral Pathology; Richard T. Glass, DDS, PhD, Steven R. Carson, DDS, MEd, Robert L. Barker, PhD, Stephnen C. Peiper, MD, Stewart Shapiro, DMD MScH, PhD; detection of HIV proviral DNA on toothbrushes: a preliminary study; ODA Journal, Winter 1994; pp. 17–20.

Oral Pathology; Sterilization By Microwaves; by Michael D. Rohrer, D.D.S., M.S. and Ronald A Bulard, B.S.; ODA Journal/Winter 1985;; p. 2931.

Microbial Contamination of Toothbrushes; Michael B. Dayoub, David Rusilko and Arthur Cross; Department of Microbiology, Division of Basic Sciences, United States Army Institute of Dental Research, Walter Reed Army Medical Center, Washington, D.C. 20012, U.S.A.; p. 706 J. Dental Research, Jun. 1977, vol. 56, No. 6.

National Oral Health Information Clearinghouse; Clinical Practice Guidelines Are Now Available Through NLM's New Full–Text Retrieval System; p. 8 No Date Available.

Zolnowski–Casey, "An Infection Control Procedure That is the Patient's Responsibility", JADA, vol. 129, pp. 616–617, May 1998.

Glass, "Toothbrush Care", Letters, JADA, vol. 129, p. 1076, Aug., 1998.

5,919,416

STERILIZATION PROCESS FOR THERMOPLASTIC APPLIANCES

FIELD OF INVENTION

The present invention relates generally to the field of sterilization processes. In preferred forms, the present invention relates to processes by which appliances (e.g., toothbrushes and other dental tools, hair brushes, combs and the like) which are entirely, or include components, formed of thermoplastic materials may be sterilized.

BACKGROUND AND SUMMARY OF THE INVENTION

It is well known that unsterile toothbrushes may contribute to the spread of disease. (Glass et al, "Toothbrush Contamination: A Potential Health Risk?", *Quintessence International*, vol. 17, No. 1, pp 39–42, 1986.) It is also well known that toothbrushes can be sterilized by exposure to microwave energy. (Rohrer et al, "Sterilization by Microwaves", ODA Journal, pp 29–31, Winter, 1985.) However, such exposure to microwave energy for prolonged time periods results in distortion and/or deformation of the nylon tooth brush bristles. (See, U.S. Pat. No. 5,040,260 to Michaels at column 1, lines 46–46.) If exposed to microwave energy for time periods insufficient to distort the nylon bristle, however, there is a risk that the toothbrush will not be sterilized.

It would therefor be highly desirable if a process were provided which enabled microwave energy (with its time-saving benefits) to be employed as a means of sterilizing thermoplastic appliances, particularly nylon-bristle toothbrushes, without distortion. It is towards fulfilling such a need that the present invention is directed.

Broadly, the present invention is embodied in a process by which microwave energy may be employed to sterilize thermoplastic appliances without distortion. According to the present invention, an appliance which is entirely, or includes components, formed of a thermoplastics material, e.g., conventional manual nylon-bristle toothbrushes or motor-assisted toothbrushes having metal components enclosed in a thermoplastics material (such as ORAL-B® toothbrushes or INTERPLAK® toothbrushes), may be sterilized by first bringing water contained in a reservoir of an uncovered sterilization tray to, or near, its boiling point by initial exposure to microwave energy. Thereafter, the appliance is placed in the sterilization tray in proximity to the microwave-preheated water. The sterilization tray may then be covered and subjected to an additional (shorter) cycle of microwave energy. During this subsequent microwave cycle, the water in the reservoir boils so that steam fills the covered container. The container is minimally pressurized by the steam (e.g., to less than about 10 psig, and usually less than 5 psig, due to the fact that the container's cover forms a fluid-tight seal). The steam and the microwave energy are sufficient to sterilize the toothbrush bristles. At the same time, however, since the time period during which the bristles of the toothbrush are exposed to the microwave energy is relatively short, no bristle deformation occurs. Alternatively, a damp toothbrush can be placed in a microwave device for longer periods of time without bristle deformity since the moisture on the damp toothbrush provides a source of steaming.

Further aspects and advantages of this invention will become more clear after careful consideration is given to the following detailed description of the preferred exemplary embodiments thereof.

BRIEF DESCRIPTION OF THE ACCOMPANYING DRAWINGS

Reference will hereinafter be made to the accompanying drawings wherein like reference numerals throughout the various FIGURES denote like elements and/or steps, and wherein;

FIG. 1 is a side elevational view, partly in section, of one possible sterilization tray that may be employed in the practice of this invention; and FIG. 2 is a block flow diagram which graphically depicts the principal steps involved in the process of the present invention.

DETAILED DESCRIPTION OF THE DRAWINGS

In the accompanying drawings and in the discussion which follows, a toothbrush has been depicted and described as one particularly preferred appliance that may be sterilized by the process of the present invention. However, it should be realized that other appliances entirely, or having components, formed of a thermoplastics material (e.g., other dental tools, hair brushes, combs, pacifier, baby bottle nipples and the like) may likewise benefit from the process of this invention. Thus, although reference has been, and will hereinafter be made to "toothbrushes", it should be kept in mind that such reference is intended to refer to a particularly preferred form of appliance that may be sterilized by the process of this invention and is non-limiting with respect thereto.

Figure 1:
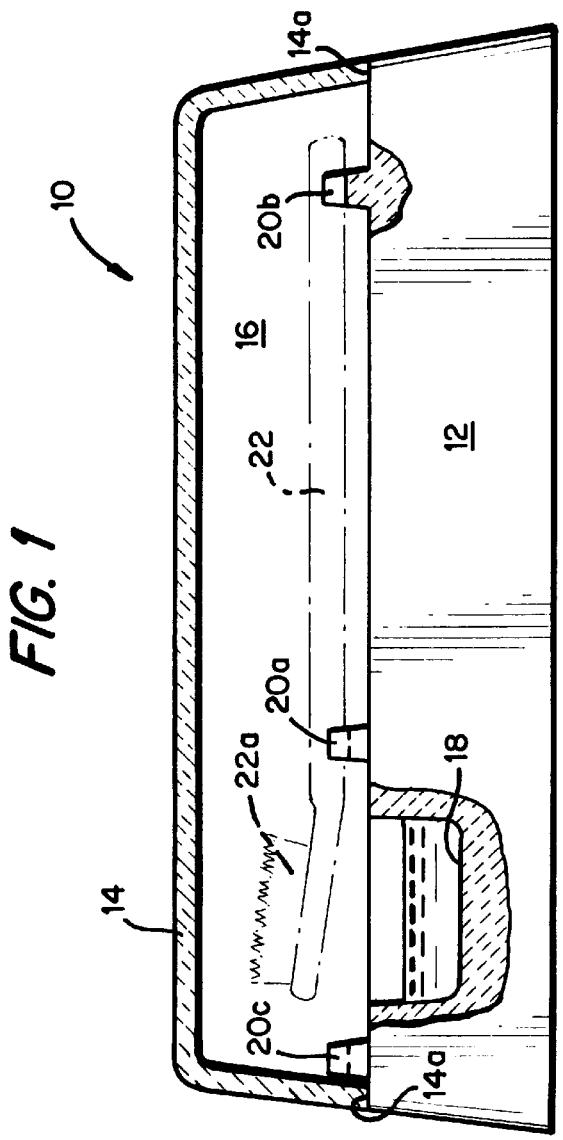

A sterilization tray 10 which may be employed in the practice of this invention is shown in accompanying FIG. 1. As can be seen, the sterilization tray 10 includes a base 12 and a cover 14 which establish therebetween a sterilization chamber 16. The base 12 and cover 14 are formed of a material capable of withstanding microwave energy without generating large amounts of heat. Preferably, the base 12 and cover 14 are formed of a material which is generally "transparent" to microwave energy (i.e., microwave-lucent), such as glass, ceramic or the like. Most preferably, the base 12 is formed of a ceramic material while the cover 14 is formed of a transparent or translucent glass material. However, the base 12 and/or cover 14 may also be formed of a plastics material provided its melting point is sufficiently high to withstand the elevated temperatures during use. One suitable class of plastics material includes polyolefins, such as polypropylene.

The base 12 is provided with a well 18 in which a quantity of sterilization fluid (e.g., water) is placed. The upper surface of the base 12 most preferably includes an aligned series of support cradles 20a, 20b which is employed to support the particular appliance in need of sterilization which, in the case depicted in FIG. 1 is a conventional toothbrush 22 having thermoplastic (e.g., nylon) bristles 22a. A further support cradle 20c may also be provided in alignment with cradles 20a, 20b so as to accommodate other types of appliances.

The lower edge 14a of the cover 14 is seated against the rim of the base 12 so that the weight of the cover 14 forms a slight seal therewith. In this regard, the weight of the cover 14 allows for slight (but meaningful) steam pressurization within the chamber 16 to occur during the sterilization process, usually on the order of less than 10 psig, and more typically less than about 5 psig. The pressure within the chamber is, moreover, self-regulating by virtue of the cover being lifted somewhat in an overpressure situation to allow steam to escape between the edge 14a and the rim of the base 12. When the overpressure situation has been relieved by the escape of steam, the weight of the cover 14 will again establish a seal between its edge 14a and the rim of the base 12.

Figure 2:
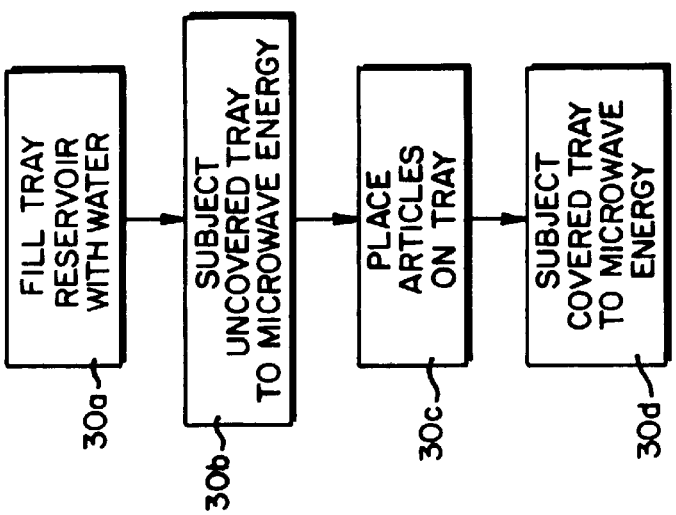

Accompanying FIG. 2 depicts in graphical fashion the preferred flow chart for practicing the process of this invention. As shown, the initial step in the process (designated step 30a) is to fill the tray reservoir 18 with a sufficient amount of water (or other sterilization liquid). The amount of the water is not critical, but a sufficient volume should be provided so as to ensure that not all of the water will vaporize during the process. Otherwise, the beneficial attributes of the steam which is generated according to the process of this invention may be minimized. For most applications, the volume of water is most preferably about 1 ounce.

The water-filled tray 10 is then placed covered in a conventional microwave oven (e.g., a household microwave oven having a nominal high power setting of about 700 watts). The oven is operated on its high power setting for a time sufficient to raise the temperature of the water to at, or near, its boiling point (preferably, ±10° C., and more preferably ±5° C. of the boiling point of the water). Typically, under standard atmospheric pressure and temperature conditions, using a nominal high power setting of about 700 watts, the water in the reservoir 18 will be heated to its boiling point after being exposed to the microwave energy for about 30 seconds. Preheating of the water will depend in large part upon the power rating of the microwave oven. For conventional microwave ovens having a nominal high power setting of between 500–1000 watts, the water will typically be preheated to boiling after about 15 seconds to about 90 seconds exposure to the microwave energy.

The toothbrush 22 is then placed onto the support cradles 20a, 20b in step 30c in such a manner that the bristles 22a are in juxtaposed relationship above the water in the reservoir 18. The tray base 12 is then covered with the cover 14. The thus covered tray 10 is thereafter placed in the microwave oven and subjected to an additional cycle of microwave energy. During this second cycle of microwave energy, the preheated water in the reservoir boils quickly and fills the chamber 16 with steam. In this regard, since the cover 14 makes a fluid-tight seal with the base 12, the steam pressurizes the chamber 16 to an extent of less than about 10 psig, and usually less than about 5 psig. Most preferably, the microwave energy is applied during the second cycle for a period of no more than about 30 seconds, typically no more than about 20 seconds. Thus, since the bristles 22a of the toothbrush 22 are exposed to the microwave energy only during the relatively short (i.e., as compared to the water preheat cycle) time period, they are not distorted and/or deformed. The heat of the steam within the chamber 16 during this second cycle coupled with the heat generated by the microwave energy per se will, however, be sufficient to thoroughly sterilize the toothbrush bristles 22a.

The procedure described above has been with regard to a toothbrush that is essentially dry prior to treatment. However, the procedure may also be employed for recently rinsed or used toothbrushes, in which case such damp bristles may tolerate longer microwave heating times. In this regard, microwave heating times of less than about 120 seconds, usually less than about 80 seconds, are typically needed and do not cause dangerous elevations of temperatures which might cause deformation of the microwave-lucent plastics material. The cover 14 is thereafter removed from the base 12 and the now sterilized toothbrush may be removed from the support cradles 20a, 20b.

The present invention will be further illustrated by the following non-limiting Examples.

EXAMPLES

Example I

An inoculate was cultured from five plastic wrapped toothbrushes after exposing the bristles thereof to a standard culture of Group A Beta Strep. The toothbrushes were, inoculated onto a new blood agar and Strep grew persistently. The inoculated toothbrushes were then subjected to steam and microwave energy in the device depicted in FIG. 1. Following such steam and microwave energy treatment, there was no growth observed. One colony of Staph Epidermitis was observed after treatment, but this was believed to be due to the unsterile storage method (i.e., on paper towels in a drawer) which was employed rather than from incomplete sterilization from the steam and microwave energy treatment.

Example II

A used toothbrush was examined and showed a baseline culture of mixed flora. The toothbrush was then subjected to steam and microwave energy treatment. After such treatment, there was no growth. In addition, a swab of the inside of the sterilization device did not grow any bacteria after treatment.

Example III

Four (4) toothbrushes were subjected to 50 cycles of 20 second microwave exposures, with no bristle deformity, with 15 seconds, approximately, between sterilization tests. Only minimal toothbrush temperature elevation during such treatments was observed.

Example IV

Three (3) additional toothbrushes were exposed to Group A Beta Strep, from the standard culture of Example I. The toothbrushes were damp and were exposed to between 90 to about 120 seconds of microwave energy using a dish similar to that shown in FIG. 1, but constructed of injection molded polypropylene (melt temperature of approximately 400° F.). The device employed a caulking material so as to seal the edges. Plating of the toothbrushes on blood and chocolate plates after treatment did not yield any bacterial growth.

Example V

A toothbrush used about 24 hours previously was dried and showed a baseline mixed flora culture, probably mostly Gamma Strep. After treatment in accordance with Example IV, no bacterial growth on chocolate or blood plates was observed.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A process for sterilizing thermoplastic appliances without distortion and/or deformation comprising the sequential steps of:

(a) placing a sterilization liquid within a sterilization tray (b) preheating the sterilization liquid by subjecting the sterilization tray and sterilization liquid therein to a microwave energy cycle in the absence of a thermoplastic appliance in need of sterilization for a time sufficient to elevate the temperature of the sterilization liquid to approximately its boiling point;

(c) placing the thermoplastic appliance in need of sterilization on the tray and covering the tray so as to form a sealed chamber in which the thermoplastic appliance is supported in proximity to the preheated sterilization liquid; and then (d) subjecting the covered tray containing the thermoplastic appliance and preheated sterilization liquid within the sealed chamber thereof to another cycle of microwave energy for a time sufficient to vaporize a portion of the sterilization liquid to cause the chamber containing the thermoplastic appliance to be pressurized to achieve a normal pressure condition of less than about 10 psig and thereby sterilize the thermoplastic appliance without distortion and/or deformation thereof.

2. The process of claim 1, wherein step (a) is practiced to elevate the temperature of the sterilization liquid to within at least "10° C." of its boiling point.

3. The process of claim 1, wherein the sterilization liquid is water.

4. The process of claim 1, wherein step (c) is practiced so as to establish a fluid-tight seal.

5. The process of claim 4, wherein said tray includes a reservoir containing said sterilization liquid, and wherein said thermoplastic appliance is supported on cradle supports within said tray above said reservoir of said sterilization liquid.

6. The process of claim 4, further comprising the step of:

(d) regulating the normal pressure condition within said chamber to less than about 10 psig during said another cycle of microwave energy by providing a cover of sufficient weight to form a seal with said tray during said normal pressure condition, but insufficient to prevent the cover being lifted in response to an overpressure condition within said chamber to allow vaporized sterilization liquid to escape from said chamber and thereby relieve said overpressure condition, following which the weight of the cover reestablishes said seal with the tray.

7. A process for distortion-free sterilization of a toothbrush having thermoplastic bristles comprising:

(i) providing a sterilization tray having a recessed well;

(ii) filling the recessed well with an amount of water sufficient to provide a reservoir of sterilization liquid during sterilization;

(iii) preheating the water in the well to approximately its boiling point temperature by subjecting the tray with its water-filled well to a first cycle of microwave energy in the absence of said the toothbrush;

(iv) placing the toothbrush with thermoplastic bristles onto the tray so that the bristles are disposed above said water-filled well;

(v) covering the toothbrush on the tray and the water-filled well thereof with a cover so as to establish a sealed chamber with said tray which contains said toothbrush and said water-filled well;

(vi) subjecting the covered tray to a second cycle of microwave energy sufficient to covert some of the water in the well to steam and thereby pressurize the sealed chamber to a normal pressure condition of less than about 10 psig, and allowing the toothbrush bristles to be exposed to the steam and microwave energy within the pressurized chamber during said second cycle for a time sufficient to sterilize the same without distortion.

8. The process as in claim 7, wherein step (v) is practiced so as to establish fluid-tight seals between the tray and the cover to thereby allow the steam to pressurize said sealed chamber.

9. The process of claim 7, wherein step (iii) is practiced so as to bring the temperature of the water in the well to ±10° C. of its boiling point.

10. The process of claim 7, wherein the toothbrush bristles are nylon.

11. The process of claim 7, wherein step (iv) is practiced by supporting said toothbrush in support cradles.

12. The process of claim 7, wherein said tray is formed of a substantially microwave transparent material.

13. The process of claim 7, wherein said tray is formed of a ceramic material.

14. The process of claim 7, wherein said tray is formed of a plastics material.

15. The process of claim 7, wherein step (v) is practiced using a cover which bounds said toothbrush on said tray and said water-filled well.

16. The process of claim 15, wherein the cover is glass.

17. The process of claim 7, wherein said first cycle of microwave energy is from about 15 seconds to about 120 seconds in duration.

18. The process of claim 7, wherein said second cycle of microwave energy is no more than about 80 seconds in duration.

19. The process of claim 7, further comprising the step of:

(vii) regulating the normal pressure condition within said chamber to less than about 10 psig during said second cycle of microwave energy by providing a cover of sufficient weight to form a seal with said tray during said normal pressure condition, but insufficient to prevent the cover being lifted in response to an overpressure condition within said chamber to allow steam to escape from said chamber and thereby relieve said overpressure condition, following which the weight of the cover reestablishes said seal with the tray.

20. A process for sterilizing a thermoplastic appliance comprising the step of:

(a) placing a thermoplastic appliance in need of sterilization on a tray which contains a sterilization liquid;

(b) covering the tray with a cover so as to establish a seal with the tray and define a sterilization chamber in which said thermoplastic appliance and said sterilization liquid are contained;

(c) subjecting the covered tray containing the thermoplastic appliance and sterilization liquid within the sealed chamber thereof to a cycle of microwave energy for a time sufficient to vaporize a portion of the sterilization liquid to cause the chamber containing the thermoplastic appliance to be pressured to a normal pressure condition of less than about 10 psig and thereby sterilize the thermoplastic appliance without distortion and/or deformation thereof; and (d) regulating the pressure within said chamber to said normal pressure of less than about 10 psig during said second cycle of microwave energy by providing a cover of sufficient weight to form said seal with said tray during said normal pressure condition, the cover being lifted in response to an overpressure condition within said chamber in excess of said normal pressure condition to allow vaporized sterilization liquid to escape from said chamber and thereby relieve the overpressure condition, following which the weight of the cover reestablishes a seal with the tray.

21. The process of claim 20, further comprising preheating the sterilization liquid.

22. The process of claim 21, wherein the sterilization liquid is preheated by filling a reservoir of the tray with sterilization liquid, and then subjecting the tray and sterilization liquid in the reservoir to an initial cycle of microwave energy sufficient to bring the sterilization liquid to near boiling.

23. The process of claim 20, wherein the tray and cover are made from the same or different material selected from the group consisting of plastics, ceramics and glass.

24. A microwaveable toothbrush sterilizer comprising:

a tray formed of a microwavable material having a reservoir for containing a sterilization liquid, and cradle supports for supporting a toothbrush with thermoplastic bristles in proximity to the reservoir;

a cover member which covers the tray and establishes a chamber in which the reservoir and the cradle supports are contained; wherein said cover member is formed of a microwaveable material of sufficient weight to regulate the pressure within said chamber to a normal pressure condition of less than about 10 psig by maintaining a seal with the tray along its edge when the sterilizer is subjected to a cycle of microwave energy, but insufficient to prevent the cover being lifted in response to an overpressure condition with said chamber to allow vaporized sterilization liquid to escaped from said chamber and thereby relieve said overpressure condition therewithin, following which the weight of the cover reestablishes said seal with toe tray.

25. The sterilizer of claim 24 wherein the tray and cover are made from the same or different material selected from the group consisting of plastics, ceramics and glass.

26. The sterilizer of claim 24, wherein the cradle supports are positioned so as to support the toothbrush bristles above the reservoir.

* * * * *